US005723508A

United States Patent [19]

Healy et al.

[11] Patent Number: 5,723,508
[45] Date of Patent: Mar. 3, 1998

[54] METHOD OF FABRICATING EMULSION FREEZE-DRIED SCAFFOLD BODIES AND RESULTING PRODUCTS

[75] Inventors: Kevin E. Healy, Evanston; Kyumin Whang; Carson H. Thomas, both of Chicago, all of Ill.

[73] Assignee: Northwestern University, Evanston, Ill.

[21] Appl. No.: 591,094

[22] Filed: Jan. 25, 1996

[51] Int. Cl.$^6$ ....................................... C08J 9/26
[52] U.S. Cl. .................. 521/61; 521/64; 521/131; 521/149; 424/489; 424/501
[58] Field of Search ................ 521/61, 64, 131, 521/149; 424/489, 501

[56] References Cited

U.S. PATENT DOCUMENTS 4,818,542  4/1989  DeLuca et al. ........................ 424/491
5,100,669  3/1992  Hyon et al. ........................... 424/426

OTHER PUBLICATIONS

"A Method to Co–Dissolve Absorbable Polymers with Water–Soluble Proteins"; Healy et al.; The 19th Annual Meeting of the Society for Biomaterials, Apr. 1993.

"Boning Up: Newly Isolated Proteins Heal Bad Breaks" by Joseph Alper; Science, 263: 324–326, Dec. 1994.

"Functional Carriers for Bone Morphogenetic Proteins" by T.S. Lindholm and T.J. Gao Annales Chirurgiae Et Gynaecologiae 82:3–12, Dec. 1993.

"Low–density, Microcellular Polystyrene Foams" by J. H. Aubert and R.L. Clough Polymer, 26: 2047–2054, Dec. 1985.

*Primary Examiner*—John M. Cooney, Jr.
*Attorney, Agent, or Firm*—Tilton Fallon Lungmus

[57] ABSTRACT

Scaffold bodies and methods for their fabrication are disclosed, and, more particularly, fabrication of scaffold bodies by freeze-drying emulsion of polymer solutions are disclosed.

9 Claims, 2 Drawing Sheets

METHOD OF FABRICATING EMULSION FREEZE-DRIED SCAFFOLD BODIES AND RESULTING PRODUCTS

FIELD OF INVENTION

The field of this invention is the fabrication of scaffolds, and more particularly fabrication of such scaffolds by freeze-drying emulsions of polymer solutions.

BACKGROUND OF INVENTION

Materials that serve as analogues for a native extracellular matrix may have uses in medicine or dentistry, and may aid in the reconstruction or regeneration of bone, cartilidge, liver, skin and other tissues. Polylactic acid, polyglycolic acid, poly ε-caprolactone, and their copolymers are potential materials for fabricating such analogues. These polymers degrade in the body by hydrolysis, and their degradation products can be ultimately expelled as carbon dioxide and water.

An ideal matrix for forming a bioabsorbable scaffold should have sufficient porosity for diffusion of nutrients and clearance of waste, and should have adequate mechanical stability to support and transfer loads. Important factors in determining successful regeneration of tissue and organs involve surface chemistry, porosity, micro- and macrostructure of the pores, and shape of the scaffolds. (The term "scaffold" is used herein to refer to structural bodies formed from such matrices.)

Such scaffold bodies can be used for administering osteogenic proteins, particularly bone morphogenetic proteins. Such proteins were described by Alper (1994), *Science*, 263:324–325. Morphogenetic proteins and functional carriers therefore were reviewed by Lindholm and Jao (1993), *Annales Chirurgiae et Gynaecologiae*, 82:3–12. These authors described the use of homopolymers of polylactic acid, polyglycolic acid, and polylactic acid-polyglycolic acid copolymers as scaffold materials for delivery of bone morphogenetic proteins.

Microcellular polystyrene foams having medical uses were described by Auger and Clough (1985), *Polymer* 26:2047–2054. In the process described by these authors, the polymer (e.g. polystyrene) is dissolved in a suitable solvent (e.g. cyclohexane), the solution is placed in a mold and the mold is cooled rapidly until the solvent is frozen. The solvent is then removed by freeze-drying, leaving behind the polymer solid as a foam.

Porous microspheres prepared from polymer emulsions have been proposed for use in drug delivery. (see DeLuca, et al. U.S. Pat. No. 4,818,452 and Hyon, et al. U.S. Pat. No. 5,100,669.) The cited patents are directed to the formation of microspheres rather than scaffold-type bodies. Emulsion systems are used, and the microspheres can be formed from bioabsorbable polymers. In the process described by DeLuca et al., an emulsion containing proto-microspheres in the form of dispersed droplets is subjected to the steps of partial freezing and freeze-drying.

The inventors of this application have reported on earlier research relating to the preparation of scaffolds from absorbable polymers. Healy, et al. Abstract, The 19th Annual Meeting of the Society for Biomaterials, Apr. 28–May 2, 1993, Birmingham, Ala. In the work reported, solvent systems were described for co-dissolving absorbable polymers and water-soluble proteins.

SUMMARY OF INVENTION

The method of this invention for fabricating bioabsorbable scaffolds utilizes a special emulsion system. The emulsion consists of a volatile polar solvent dispersed in a non-polar volatile solvent. These solvents are immiscible. The non-polar solvent contains a biocompatible polymer which is soluble therein while being insoluble in the polar solvent. Where scaffolds prepared from the emulsion are to be used for delivery of therapeutic agents, the agent is either dissolved in the dispersed polar, or if the agent is soluble therein, in the nonpolar phase.

In carrying out the method of this invention, an emulsion prepared as described, is frozen to a completely solid condition. Both the dispersed phase and the continuous phase solvents are converted to solids by rapid freezing. This freezing is done without breaking the emulsion or throwing the polymer out of solution.

As the next step in the process, the completely frozen emulsion is subjected to freeze-drying to remove the solvents thereby converting the dissolved polymer to a solid condition. The polymer solids are thereby formed into porous open-celled bodies.

With the method of this invention, the porous scaffold bodies can be formed in molded shapes or in standard shapes for later cutting. This is accomplished by introducing the emulsion into a mold which is then subjected to the freezing and freeze-drying steps. The resulting structures can have sufficient strength to be useful in medical applications such as bone implants (i.e. grafts). The microarchitecture (i.e. pore size, porosity, and specific surface area) can all be controlled by altering processing variables. Scaffolds can also be cut at the time of use to adapt to specific geometries.

A water soluble therapeutic agent may be incorporated in the dispersed polar phase. The freeze-drying step will tend to distribute therapeutic agents within the polar phase and possibly into the resulting polymer structure so that it can be extracted when the scaffold body is implanted. A sustained rate of release of the therapeutic agent can be obtained with the initial release being at a higher rate. Apparently the therapeutic agent tends to be concentrated on or in the exposed surfaces of the porous body. Introduction of the agent into the polar phase, phase separated from the non-polar phase, is believed to be desirable in protecting the agent from degradation (i.e. denaturation) from any extensive contact with the nonpolar solvent.

Figure 1:
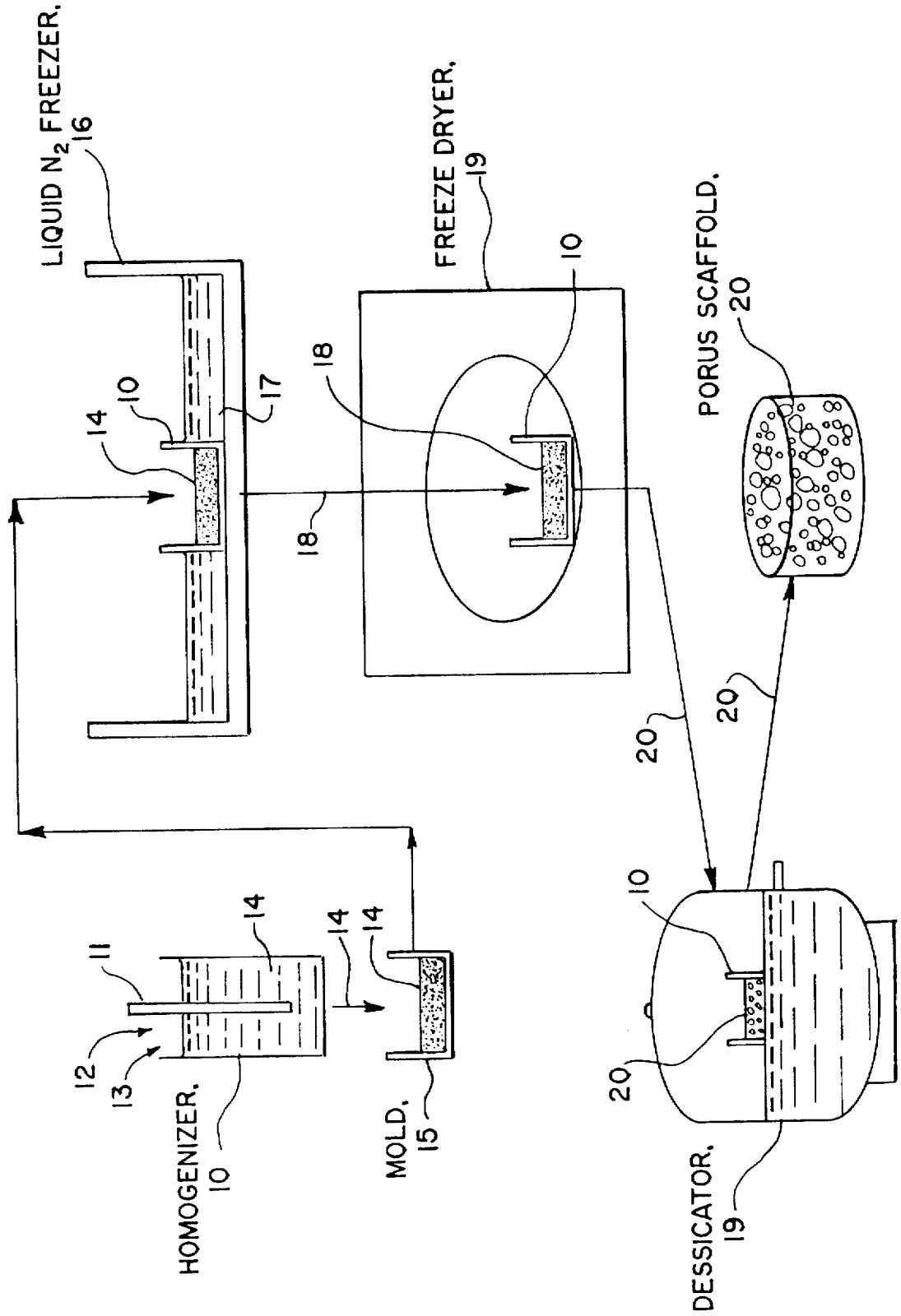
FIG. 1 of the accompanying drawing is a diagrammatic flow sheet illustrating the steps for preparing porous scaffold bodies by the method of this invention.

A homogenizer vessel (10) can be equipped with a mechanical homogenizer, or a sonicator probe, or any other means for forming an emulsion (14) from a volatile polar solvent (12) and a volatile non-polar solvent (13). A bioabsorbable polymer is dissolved in the non-polar solvent (13); and, when used, a water soluble therapeutic agent is dissolved in the polar solvent (12).

After a water-in-oil type emulsion is formed with a polar dispersed phase and a non-polar continuous phase, the emulsion is introduced into a heat-conductive mold (15), such as a copper mold. The emulsion in the mold (15) is subjected to rapid freezing in the vessel (16), wherein the mold (10) with the emulsion (14) therein is immersed in liquid nitrogen (17).

The completely frozen emulsion (18) is transferred in the mold (15) to a freeze-dryer wherein it is subjected to removal of the solvents. The resulting porous scaffold body (20) can be removed from the mold, or preferably, the molded body can be transferred to a vacuum desiccator or a vacuum oven (19) for removal of any residual solvents. The resulting product is a molded porous body (20) having an open-cell type porosity.

Figure 2:
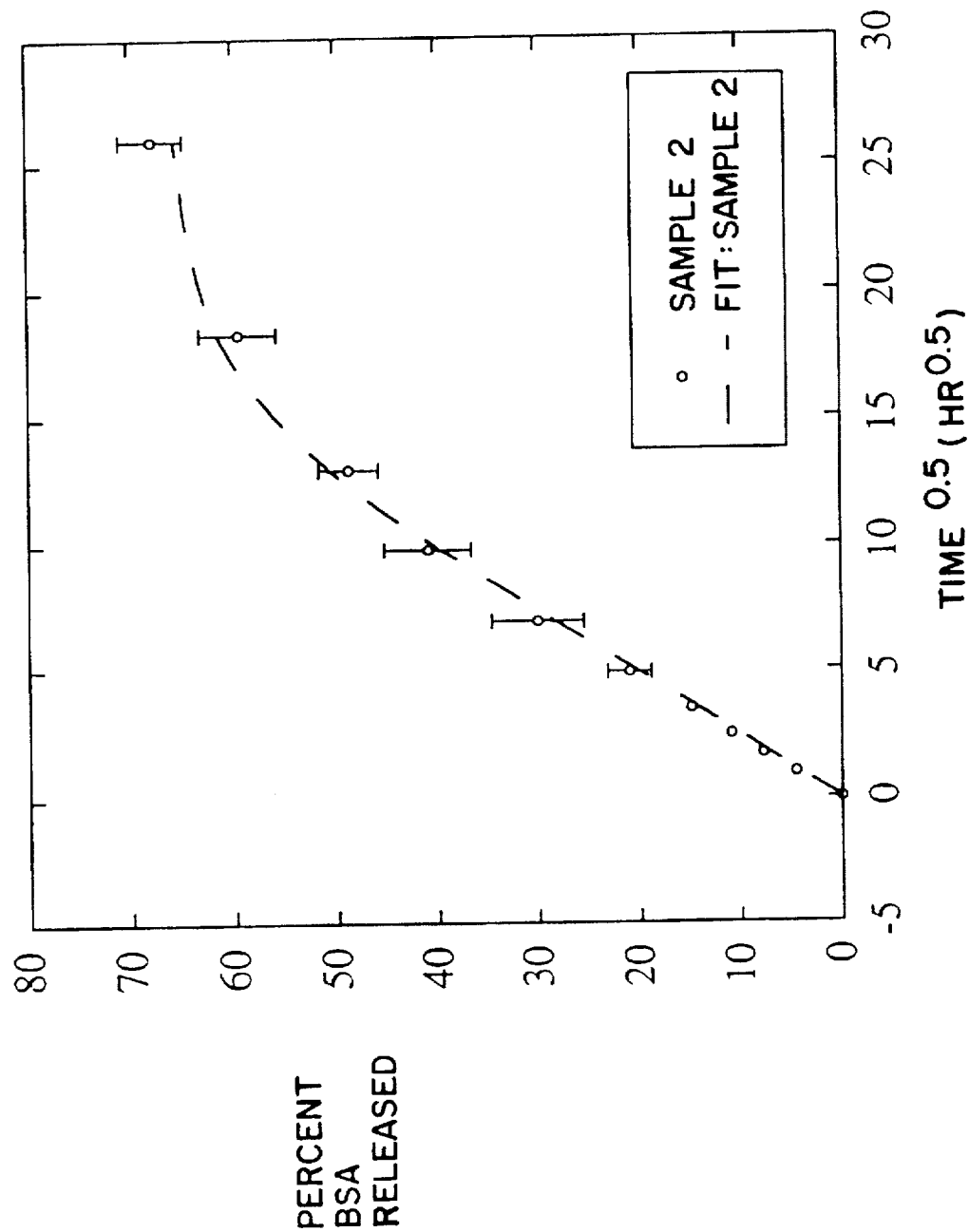

FIG. 2 is a release rate curve for a soluble protein which was incorporated in the porous body by being dissolved in the aqueous phase. (See Example IV for details.)

PREFERRED FORMULATIONS

For the purposes of this invention, one preferred emulsion system consists of water (the aqueous phase) dispersed in methylene chloride (the continuous phase). Other polar solvents can be used, such as acetic acid, methanol, ethanol, and mixtures thereof including aqueous mixtures. Also, other non-polar organic solvents can be used such as carbon tetrachloride, chloroform, cyclohexane, toluene, or mixtures thereof including mixtures with methylene chloride. Importantly, a non-polar solvent should be selected which is substantially immiscible with the polar solvent.

In certain preferred embodiments, the nonpolar solvent is more volatile or has a lower melting point than the polar solvent. This has the added advantage of removing the nonpolar solvent first while the therapeutic agent remains in the frozen polar phase when the temperature is raised slowly. Thus, the agent is further protected from the potentially harmful nonpolar phase and vapors.

The biocompatible polymer should be soluble in the selected non-polar solvent and substantially insoluble in the polar solvent. Preferred polymers, which are biocompatible and bioabsorbable, comprise polymers of polyglycolic acid, polylactic acid, and their copolymers. Other biocompatible polymers can be used, such as poly($\epsilon$-caprolactone), poly (hydroxybutyrate), and copolymers of polyesters, polycarbonates, polyacrylates, polyanhydrides, polyorthoesters, and like degradable materials, providing the selected polymer has the solubility characteristics described. Also, nondegradable polymers with similar solubility characteristics can be used.

Water-soluble therapeutic agents can be incorporated in the polar phase. For example, the therapeutic agent may be a water-soluble protein such as a bone morphogenetic protein. In a preferred embodiment, the protein or other agent is not soluble in the selected non-polar solvent so that it will remain captivated in the dispersed droplets of the polar phase. Alternatively, however, embodiments can be used in which the therapeutic agent is soluble in the nonpolar phase and insoluble in the polar phase.

With the preferred solvents and polymers, water-in-oil type emulsions form without the need for a surface active or emulsifying agent. However, to promote the formation of the desired water-in-oil type of emulsion, bio-acceptable surfactants, emulsifiers, or salts can be used, e.g. polyethylene glycol, or potassium chloride.

In general it is desirable to incorporate at least five (5) parts by weight of the bioabsorbable polymer per each one hundred (100) parts total volume of both solvents. Usually, it will not be necessary to incorporate more than 20 parts by weight of the bioabsorbable polymer per each 100 parts total volume of the solvents. However, in some embodiments, lesser or greater amounts of the polymer might be used. Nondegradable biocompatible polymers can also be used to create nondegradable scaffolds.

The relative volume of the polar and non-polar phases can be varied. In general, the emulsions can contain from about 20 to 60 parts by volume of the polar solvent per 100 total parts by volume of both solvents.

DETAILED EXAMPLES

The method of this application and the uses of the scaffold bodies prepared thereby are illustrated by the following examples.

Example I

Studies were conducted as described below using the method of this application to produce porous scaffold products from a representative bioabsorbable polymer.

Materials

DL-lactide/glycolide copolymers of 85:15 (lactide/glycolide) nominal monomer ratio, and $\eta_{inh}$ of 0.25, 0.51 and 0.79 dlg$^{-1}$ were obtained from Birmingham Polymers Inc. (Birmingham, Ala.). Methylene chloride (MC) was obtained from Baxter Diagnostics Inc. (McGraw Park, Ill.) and was used as received.

Fabrication of Scaffolds

The fabrication was carried out as described above with particular reference to the flow sheet FIG. 1. The polymer was first dissolved in MC such that it would have the desired % w/v to the total volume (5 ml) of emulsion. Appropriate volumes of the polymer-MC solution and ultrapure water (ASTM grade 1, 18M$\Omega$-cm) were added together in a glass testube so that the desired volume fraction of water ($\phi$) was achieved. The $\eta_{inh}$ and $\phi$ values of the polymer and polymer % w/v used in each sample are listed below in Table 1. The immiscible layers were homogenized, using a handheld homogenizer (Omni Int., Waterbury, Conn.), then poured into a cylindrical copper mould (internal diameter=2.54 cm; height=3 cm), and frozen rapidly by quickly placing the mould into a copper container that was maintained near liquid nitrogen temperature (--196° C.). When all the samples were frozen, they were freeze-dried (Virtis Co Inc., Gardiner, N.Y.) Samples were then placed in a vacuum desiccator at room temperature for at least 7 days to remove any residual solvent. Porous open-celled scaffold bodies were obtained.

TABLE 1

Processing variables for scaffolds

| Sample | $\eta_{inh}$ (dlg$^{-1}$) | $\phi$ | Polymer (% w/v) |
|---|---|---|---|
| 1 | 0.79 | 0.4 | 10.0 |
| 2 | 0.82 | 0.5 | 7.5 |
| 3 | 0.51 | 0.4 | 7.5 |
| 4 | 0.51 | 0.5 | 7.5 |

Scanning Electron Microscopy (SEM) Analysis

After a week in the vacuum desiccator, the samples were cut in half using a sharp razor blade, a thin piece was sheared from the center, sputtered with gold (SCD 040 sputter machine, Blaxers, Conn.), and observed using SEM.

Mercury Porosimetry Analysis

Samples were analyzed by mercury porosimetry using an AutoPore II 9220 (Micromeritics, Norcross, Va.) to determine pore size distributions, specific pore area, median pore diameter and porosity. A solid penetrometer volume ranging from 6.7 to 7.3 ml and samples weighing about 0.1 g were used. Mercury was filled from a filling pressure of 3.4 kPa (0.5 psia) and intruded to a maximum pressure of 414 MPa (60,000 psia). The relationship between the filling pressure and pore radius is given by the Washburn equation:

$$r = -2\gamma \cos(\theta)/P$$

Where $\gamma$ is the surface tension of mercury (~480 dyne cm$^{-1}$) and $\theta$ is the contact angle between mercury and the polymer surface. This equation gives the corresponding radius of a cylindrical pore. The sessile drop contact angel between mercury and a solvent-cast PLGA film was measured with a customized micrometer microscope fitted with a goniometer eyepiece (Gaertner, Chicago, Ill.) at ambient temperature. The three-phase contact angle between the liquid (mercury), vapor and the surface (polymer) was 137°±1° (n=4), and was used to calculate the pore diameter from the intrusion pressure.

Mercury was intruded from a filling pressure of 0.5 to 60,000 psia. There were pores greater than 200 μm in all three samples and a clear distinction of two types of pores were seen (d>1 μm and d<0.1 μm). A broad distribution of pores was also evident. The mercury porosity results are summarized below in Table 2.

TABLE 2

Mercury porosimetry results

| Sample | Porosity (%) | Median pore size (μm) | Specific pore area ($m^2g^{-1}$) |
|---|---|---|---|
| 1 | 91 | 35 | 58 |
| 2 | 89 | 52 | 17 |
| 3 | 93 | 15 | 99 |
| 4 | 90 | 9 | 16 |

Discussion of Results

Scanning electron micrographs of the three different scaffolds were made. Even though there was a large distribution of pore size for a given sample, clear differences in the average pore sizes were evident, with sample 2 having the largest pores and sample 4 having the smallest. All samples were highly porous with good interconnections between pores, and they were physically stable and manageable.

The mercury porosimetry analysis demonstrated the ability of the fabrication technique to create scaffolds with high porosity and varying pore size. These samples gave average porosities ranging from 89 to 93%, median pore sizes ranging from 9 to 52 μm, and specific pore areas ranging from 16 to 99 $m^2g^{-1}$ (Table 2). However, the largest pores were greater than 200 μm in all the samples. This distribution of pore sizes was also observed in the micrographs. There was also a clear distinction of two types of pores: those larger than about 1 μm were thought to be mostly due to the emulsion while the much smaller pores were probably due to the inherent porosity of the polymer itself from the evaporation of the solvent, similar to those found in phase-separated foams. These results verify the influence that varying processing variables have on scaffold properties, i.e. porosity, pore size distribution and specific pore area.

Example II

One of the purposes of this invention was to develop a method for processing biodegradable polymer scaffolds to be used as devices that stimulate tissue regeneration. Scaffolds fabricated using the emulsion freeze-drying method as described herein were tested in vitro to see if they were suitable for tissue engineering and regeneration. Cells were seeded onto scaffolds with 35 μm median pore size in vitro and were tested for cell proliferation using the 3-(4,5-dimethylthiazol-2-yl)-2,5-diphenyl tetrazolium bromide (MTT) assay and for cell phenotypic expression using the alkaline phosphatase assay. Processing parameters were varied to produce scaffolds with varying pore sizes. Scaffolds proved to increase cell proliferation over tissue culture polystyrene (TCPS). These results are novel in that the method to fabricate these scaffolds and their microarchitecture are novel, and prove that the emulsion freeze-drying process is suitable for fabricating scaffolds useful for tissue regeneration.

Use of Scaffolds for In Vitro Cell Proliferation

This experiment investigated the effect of the scaffold on in vitro cell proliferation. Pilot studies have shown that the total number of cells can be estimated via the use of the MTT assay and with a few minor modifications, the polylactic-coglycolic acid (PLGA) scaffolds do not interfere with the assay. The MTT assay uses a colorimetric detection method which reads the amount of formazan in the cells. Alkaline phosphatase assay was used to confirm cell behavior. Alkaline phosphatase assay is a colorimetric assay that detects the release of P-nitrophenyl phosphate (pNPP) bound to the alkaline phosphatase synthesized by osteoblasts (or osteoblast-like cells) and released into solution.

Scaffold Processing

The PLGA scaffolds for the in vitro experiments were fabricated as described in Example I using polymers with $\eta_{inh}$=0.79 dL/g. 0.5 g of polymer was dissolved in 3 ml of methylene chloride (MC) (10% w/v of emulsion) and homogenized to form an emulsion with 2 ml of water (φ=0.4). The emulsion was poured into a cylindrical mold and frozen rapidly in liquid nitrogen. The frozen emulsion was then freeze-dried.

Cell Harvest and Seeding

The cells used were isolated using the procedure of S. W. Whitson, et al., *J. Bone Miner. Res.* 7:727–741 (1992). The calvaria of 6 to 12 day old Sprague-Dawley rats were used. Bone cell isolation was performed with an enzymatic digestion in Dulbecco's modified eagle's media (DMEM; Gibco, Grand Island, N.Y.) containing 3 mg/ml dispase and 0.5 mg/ml collagenase (Sigma Chemical Company, St. Louis, Mo.). Contents of the digestion were spun down, the pellet resuspended, and the resulting cells incubated at 37° C. with 5% $CO_2$, 95% air, and 99% relative humidity. Cells were fed twice weekly and used in this experiment between passages 2 and 4. Growth media containing DMEM, 15% heat-inactivated fetal bovine serum (FBS), 1% penicillin-streptomycin, 1% fungizone, Hepes buffer (15 mM), sodium pyruvate (1 mM) and ascorbic acid (5 μg/ml) was used to maintain cells.

Two sets of four scaffolds with 91% porosity and pore size of 35 μm were used to seed cells. The scaffolds were sterilized and wet by immersing in 70% ethanol solution for one hour and then rinsing twice with PBS (phosphate buffer solution). On the first set, approximately $4 \times 10^4$ cells were pipetted and seeded; the second set contained approximately $8 \times 10^4$ cells. These scaffolds were then put in growth media to allow cell growth. Four additional scaffolds were not seeded with cells, but maintained in media to be used as negative controls to verify that the scaffold did not interfere with the assays. Cells were also seeded onto two sets of four tissue culture polystyrene (TCPS) dishes as positive controls for in vitro cell proliferation. Again, one set was seeded with approximately $4 \times 10^4$ cells and the second with approximately $8 \times 10^4$ cells. Four other TCPS not seeded with cells were used as negative controls to confirm that there was no interference with the assay. The TCPS samples were also put in growth media to allow cell growth. Aliquots of the supernatant for the alkaline phosphatase assays were taken and analyzed at 3 day, 6 day, and 7 day intervals, while the MTT assay was performed at only 7 days after cell seeding. The control groups were also analyzed to verify that there was no interference of the polymer nor the TCPS to the assays as well as check the level of noise.

Alkaline Phosphatase Assay

This assay measures the total alkaline phosphatase present in the supernatant. Along with the MTT assay, the presence of osteoblasts and an estimation of the number of viable osteoblasts can be established. Alkaline phosphatase assay is an established method [O. A. Bessey, et al., *J. Biol Chem.*, 164: 321–329 (1946)], and showed whether any alkaline phosphate was secreted by the cells, which is indicative of an osteoblast population.

MTT Assay

The MTT was dissolved in PBS at a concentration of 5 mg/ml. 0.1 ml of this solution was added to wells with 2.4 ml of fresh DMEM media, and left for 24 hours in 37° C. The scaffolds were then washed twice with 10 ml of PBS followed by an addition of 3 ml of dimethyl sulfoxide (DMSO). DMSO dissolves the formazan crystals releasing the bound MTT as a blue color. Due to the cells being inside the scaffold, the seeded scaffolds were then manually crushed with glass rods and centrifuged to separate the cells from the scaffolds. Finally, the supernatant was pipetted onto a 96 well plate in triplicate, and read using an ELISA plate reader at a wavelength of 562 nm. The assay turned blue with the presence of viable cells and the absorbance of the supernatant at a wavelength of 562 nm gave an estimate of the number of cells. The absorbance readings for the controls, which remained clear, was used as background absorbance and subtracted from the sample absorbance readings. The results were analyzed to see whether the presence of the scaffold significantly affected the growth of cells in vitro using the Analysis of Variance (ANOVA) with a Neuman-Keuls post-hoc test.

Results

In the alkaline phosphatase assays, all negative controls showed neither alkaline phosphatase synthesis nor interference with the assay. Alkaline phosphatase was detected in a manner consistent with an osteoblast population. Initial values of alkaline phosphatase were low, but by day 7 significant amounts of alkaline phosphatase were secreted.

In the MTT assay, at the lower initial cell seeding density, there was no significant difference between cells seeded on the polymer scaffold vs. TCPS. At the higher initial cell density, there was a significant increase at a $p<0.005$ level in cell proliferation for cells seeded on scaffolds vs. TCPS. All negative controls showed neither cell proliferation nor interference with the assay.

These results demonstrated that the PLGA scaffolds fabricated by the method of this application are suitable for in vitro tissue engineering and are statistically better in promoting cell proliferation, which is probably due to the large surface area of the scaffold (i.e. microarchitecture).

Example III

Intraosseous critical-size defects (CSD's) used in species ranging from rodents to nonhuman primates have been found to be the most reliable in evaluating bone regeneration via growth factors, delivery systems, and other devices like scaffolds. A CSD may be defined as the smallest intraosseous wound that will not regenerate completely with new bone, and less than 10% of the original osseous contour will be regained in the lifetime of the animal. Models can include rat, rabbit and dog calvaria, mandible and long bone CSD's.

The rat CSD was chosen for the in vivo bone regeneration experiment because it is unlikely that bone bridging will occur within 6 months, and the CSD will remain relatively constant throughout the lifetime of the animal. In the rat calvaria model, the CSD is defined to be 8 mm defects created in the parietal bones. Mature animals should be used because skeletally immature animals heal more completely and rapidly in general. Analysis of bone regeneration must be validated radiographically through radiographic evidence of closure of the epiphyseal plates. This model has become a standard for screening devices for bone regeneration. [Hollinger, J. O. 'Animal models for assessing bone repair with emphasis on Poly($\alpha$-hydroxy acid) deliver systems.' In: Brighton, C. T., Friedleander, G. E., Lane, J. M. (eds.). Bone Formation and Repair, Academic Academy of Orthopaedic Surgeons, Rosemont, Ill. 1994. pp. 341–353.]

Scaffold Processing

PLGA scaffolds with large (32 μm) and small (16 μm) median pore sizes for the in vivo experiments were fabricated as described in Example I using polymers with $\eta_{inh}=$ 0.82 dL/g. 0.375 g of polymer was dissolved in 3 ml of methylene chloride (MC) (7.5% w/v of emulsion for the small pore sized scaffolds and 10% w/v for the large pore sized scaffolds) and homogenized to form an emulsion with 2 ml of water ($\phi=0.4$). The emulsion was poured into a cylindrical mold and frozen in liquid nitrogen. The frozen emulsion was then freeze-dried.

All the large and small pore sized scaffolds were cut into 8 mm diameter discs to fit into the CSD and sterilized with gamma radiation.

Rat CSD Surgical Procedure

Sprague-Dawley rats, approximately 6 months old and 300 g, were purchased from Harlan Sprague-Dawley (Indianapolis, Ind.). Rats were anesthetized with interperitoneal injections of pentobarbital 50 mg/kg. Mid-sagittal incisions were made and carried down to the calvarium. Scalp flaps were reflected laterally, exposing the frontal and parietal portions of the cranium. The overlying parietal periosteum were excised and 8 mm diameter circular defects were made in the cranium using a dental bur. Five large and small median pore-sized scaffolds were implanted in the CSD's and left to heal for 8 weeks. Positive control consisted of 5 CSD's replaced with excised calvaria and negative controls consisted of 5 CSD's left unreplaced. After 8 weeks the rats were sacrificed, the calvaria excised, and contact radiographs taken at the Northwestern Memorial Hospital.

Radiomorphometry

The amount of bone growth was quantitated by scanning the radiographs of the scaffolds into a computer using an imaging densitometer at a resolution of 64 μm. The scanned image was thresholded using Adobe Photoshop® to show black for the uncalcified area and white for the calcified area. The area of calcified tissue was determined with Adobe Photoshop®. Pilot studies have confirmed that these scaffolds do not appear on the radiographs.

Histologic Analysis

Histology was performed at the Genetics Unit, Shriners Hospital for Crippled Children (Montreal, Canada) to confirm the presence of bone and evaluate the biocompatibility of the scaffold. Excised samples were fixed in phosphate buffer for 24 hours twice, rinsed in varying concentrations of alcohol several times, and then in xylene twice to dehydrate the sample. Finally, the samples were infiltrated with methyl methacrylate and polymerized for 2 weeks. Once the samples were processed, they were sectioned into 6 μm layers and deplastified before staining with Goldner Trichrome leaving the mineralized matrix dark green, and the osteoid, marrow and vascular tissue red. The scaffold alone was also stained with the same procedure to verify that the polymer did not interfere with the stain. The stained sections were analyzed under light microcopy to identify bone and other tissues.

Results

The radiomorphometry results of contact radiographs of the CSD's with a) negative controls, b) positive controls, c)

small pore sized scaffolds, and d) large pore sized scaffolds were observed. Though the CSD's with the scaffolds did not heal completely within 8 weeks, and so have significantly less bone as compared to the positive controls, it is clearly seen that there were more bone than the negative controls. About 60%±20% of the defect was incorporated with new bone for the small pore sized scaffold groups, and 50%±30% for scaffolds with large pore size; there was no statistical difference between these two groups probably due to the large pore size distributions of both sets of scaffolds. The negative controls however did have some new bone growth, about 30%±4%. The short duration of the experiment (8 vs. 12 or 16 weeks) may have affected the significance of the results since the wound did not have enough time to heal completely. It is interesting that scaffolds with median pore sizes less than 150 µm were able to promote bone regeneration, which is contradictory to literature reports citing that at least 150 µm was necessary.

The histological analysis confirmed that new bone formation occurred in the CSD's with scaffolds. These results showed that PLGA scaffolds fabricated with the emulsion freeze-drying method of this incentive are suitable for in vivo bone regeneration. While there was no statistical difference in bone growth between the two different pore sizes, there was substantial bone ingrowth which was unexpected in a device with median pore sizes below 150 µm. However, literature citing a requirement of 150 µm for bone growth may be inaccurate due to the presence of micromotion (which is approximately±50 µm), thus a much lower median pore size may be needed for applications where there is no micromotion. Furthermore, the pore size distribution is very large in the scaffolds used here, with some pore sizes larger than 200 µm. This wide distribution may be beneficial, allowing applicability to different types of tissues. In short, the novel scaffold microarchitecture, i.e. pore size, pore size distribution, porosity and specific surface area make this material unique and allows bone regeneration in sub 150 µm pore-sized scaffolds.

Example IV

The use of scaffold bodies prepared as described in the foregoing examples for delivery of water-soluble proteins was studied using bovine serum albumin as a representative protein.

Methods

Methods to produce two different pore sized PLGA scaffolds were modified to incorporate and release bovine serum albumin (BSA). Pore size was controlled by varying one or more of the processing variable: polymer inherent viscosity ($\eta_{inh}$); volume fraction of the dispersed phase (water) ($\phi$); and, polymer weight-to-volume percent (% w/v) (Table 3). Protein was incorporated into the scaffold by dissolving it in the water phase. Thus, the protein was phase separated from the organic solvent during processing. To fabricate the scaffolds, PLGA (85:15; D,L-lactide:glycolide) with various $\eta_{inh}$ were dissolved in methylene chloride (MC). Then the two immiscible layers of PLGA-MC and BSA-water solutions were homogenized creating an emulsion. The emulsion was rapidly cooled in liquid nitrogen to lock in the liquid-state structure, and the solvent and water were removed by freeze-drying. After freeze-drying, the scaffolds were placed in a vacuum desiccator at room temperature for at least 7 days to remove any residual solvent.

Previously, these samples were analyzed with scanning electron microscopy (SEM) and mercury porosimetry to determine the pore size distribution, median pore diameter, and porosity.

Actual loading of BSA into the scaffolds was determined by redissolving one of the scaffolds into MC, extracting the BSA out by adding excess water to form an emulsion, and measuring the protein concentration with the Coomassie Plus® Protein Assay (Pierce, Rockford, Ill.). BSA released from the scaffolds was measured over a 4 week time interval. Samples were immersed in 25 ml of PBS, pH 7.4, and 37° C. After each measurement, the surrounding fluid was replaced with new PBS to maintain sink conditions.

TABLE 3

| Scaffold Processing Variables | | | |
|---|---|---|---|
| Sample | $\eta_{inh}$ (dL/g) | $\phi$ | Polymer % w/v |
| 1 | 0.79 | 0.4 | 10.0 |
| 2 | 0.51 | 0.4 | 7.5 |

Results

Clear differences in average pore size was evident, with sample 1 having the larger pores. Characteristics of the scaffolds are shown in Table 4. Note that despite the small median pore sizes, the largest pores were greater than 200 µm. All samples were highly porous open-cell scaffolds, and they were physically stable and manageable. Scaffolds made with this method can be made thick (>1 cm).

TABLE 4

| Scaffold Characteristics | | |
|---|---|---|
| Sample | Porosity (%) | Median Pore Size (µm) |
| 1 | 91 | 35 |
| 2 | 93 | 15 |

Loading of BSA in samples 1 and 2 was determined to be 16 and 24 mg, respectively. In the release rate study, an initial burst followed by a slower release was observed, as shown in FIG. 2. About 60% of the BSA released within 4 weeks for sample 1. Sample 2 showed a much more gradual release, but matched sample 1 in total release of protein by 4 weeks. The initial release characteristics are due to the effect of pore size, indicating a diffusion-limited response. An increase in the median pore size will decrease the tortuosity created by the interconnection of the pores allowing quicker release of BSA from inside the scaffold; hence, the faster initial release from sample 1. Release curves were fitted with complete diffusion equations and showed that sample 2 was indeed diffusion controlled. Sample 1 data did not fit equations possibly due to effects of convection being more pronounced when stirring and handling in scaffolds with large pores.

Conclusions

It was evident from the SEM and mercury porosimetry results that scaffolds with differing pore sizes and high propensities were produced. Protein was also incorporated and released in a controlled manner by varying the physical characteristics of the scaffolds such as median pore size and/or polymer $\eta_{inh}$. This fabrication method can be used in a wide variety of applications where controlled site-specific delivery of macromolecules is needed to stimulate tissue regeneration.

We claim:

1. A method of fabricating a porous molded scaffold body, comprising the steps of:

(a) preparing an emulsion with a polar solvent dispersed in a non-polar solvent which is immiscible with said polar solvent, said non-polar solvent having dissolved therein from 5 to 20 parts by weight of a biocompatible polymer per each 100 parts total volume of both solvents, said polymer being insoluble in the dispersed polar solvent and forming a solid upon freeze-drying;

(b) freezing said emulsion in a mold under conditions which convert both of said solvents to solids without breaking the emulsion or throwing the polymer out of solution, thereby obtaining a solid frozen body of molded shape;

(c) subjecting the resulting molded frozen body to freeze-drying under conditions which convert the entire body to a porous solid; and (d) continuing the freeze-drying until said entire body is a porous open-celled body.

2. The method of claim 1 in which the polar solvent is water, the non-polar solvent is methylene chloride, and the polymer is selected from polylactic acid, polyglycolic acid, and copolymers thereof.

3. The method of claim 2 in which said polymer is a copolymer of polylactic acid and polyglycolic acid.

4. A method of fabricating a porous molded scaffold body for delivery of a therapeutic agent, comprising the steps of:

(a) preparing an emulsion with a polar solvent dispersed in a non-polar solvent which is immiscible with said polar solvent, said polar solvent containing a water-soluble therapeutic agent, the non-polar solvent having dissolved therein from 5 to 20 parts by weight of a biocompatible polymer per each 100 parts by volume of the total solvents, said polymer being insoluble in said polar solvent and forming a solid on removing the non-polar solvent;

(b) introducing a portion of said emulsion into a mold in which it can be frozen;

(c) freezing said emulsion in said mold under conditions which convert both of said solvents to solids without breaking the emulsion or throwing the polymer out of solution, thereby obtaining a solid frozen body of molded shape;

(d) subjecting the resulted molded frozen body to freeze-drying under conditions which remove said solvents and convert the entire body to a porous solid; and (e) continuing the freeze-drying until said body is a porous open-celled body having a molded shape.

5. The method of claim 4 in which said non-polar solvent is selected from methylene chloride, carbon tetrachloride, chloroform, cyclohexane, toluene, and mixtures thereof, said polar solvent is selected from water, acetic acid, methanol, ethanol, and mixtures thereof, and said therapeutic agent is a water-soluble protein.

6. The method of claim 4 in which the polar solvent is water, the non-polar solvent is methylene chloride, the polymer is a co-polymer of polylactic acid and polyglycolic acid, and the therapeutic agent is a water-soluble bone morphogenetic agent.

7. A method of fabricating a porous molded scaffold body, comprising the steps of:

(a) preparing an emulsion with an aqueous phase dispersed in non-polar volatile liquid solvent phase which is immiscible with water, said aqueous phase having a volume of from 20 to 60 parts per 100 total parts by volume of both the aqueous phase and the non-polar solvent phase, said non-polar solvent phase having dissolved therein from 5 to 20 parts by weight of a bioabsorbable polymer per each 100 total parts by volume of both phases;

(b) introducing a portion of said emulsion into a mold in which it can be frozen;

(c) freezing said emulsion in said mold under conditions which convert both of said phases to solids without breaking the emulsion or throwing the polymer out of solution, thereby obtaining a solid frozen body of molded shape;

(d) subjecting the resulted frozen body in said mold to freeze-drying under conditions which remove said solvents, the polymer converting to a solid condition as said non-polar solvent is removed;

(e) continuing said freeze-drying until the polymer forms into a porous open-celled body having the shape of said mold; and (f) removing the porous body from the mold to obtain the scaffold body.

8. The method of claim 7 in which the non-polar solvent is methylene chloride and the polymer is a copolymer of polylactic acid and polyglycolic acid.

9. The porous, molded scaffold bodies produced by the method of claims 1, 2, 3, 4, 5, 6, 7, or 8.

* * * * *